United States Patent
Mulholland

(10) Patent No.: US 7,618,429 B2
(45) Date of Patent: Nov. 17, 2009

(54) SKIN REJUVINATION RESURFACING METHOD

(75) Inventor: R. Stephen Mulholland, Toronto (CA)

(73) Assignee: SpaMedica International SRL, Warrens, St. Michael (BB)

( * ) Notice: Subject to any disclaimer, the term of this patent is extended or adjusted under 35 U.S.C. 154(b) by 443 days.

(21) Appl. No.: 11/315,841

(22) Filed: Dec. 22, 2005

(65) Prior Publication Data

US 2007/0149991 A1 Jun. 28, 2007

(51) Int. Cl.
*A61B 17/34* (2006.01)

(52) U.S. Cl. ............ 606/186; 606/204.15; 606/204.35

(58) Field of Classification Search ............ 606/185, 606/186, 170, 169, 172, 177, 178, 180, 183, 606/204.35, 204.15, 171; 601/84, 89, 93–95, 601/97, 107, 111; 128/907
See application file for complete search history.

(56) References Cited

U.S. PATENT DOCUMENTS

| | | | | |
|---|---|---|---|---|
| 3,193,908 A | * | 7/1965 | White | 29/81.14 |
| 3,918,449 A | * | 11/1975 | Pistor | 604/47 |
| 4,565,189 A | * | 1/1986 | Mabuchi | 601/93 |
| 5,471,102 A | * | 11/1995 | Becker et al. | 310/50 |
| 5,549,640 A | * | 8/1996 | Fontenot | 607/149 |
| 5,593,381 A | * | 1/1997 | Tannenbaum et al. | 601/93 |
| 5,968,063 A | * | 10/1999 | Chu et al. | 606/185 |
| 6,024,706 A | * | 2/2000 | Hsiao | 600/556 |
| 6,090,790 A | * | 7/2000 | Eriksson | 514/44 |
| 6,251,100 B1 | * | 6/2001 | Flock et al. | 606/2 |
| 6,699,908 B2 | * | 3/2004 | Sackler et al. | 514/563 |
| 6,960,214 B2 | * | 11/2005 | Burkinshaw | 606/79 |
| 7,066,908 B2 | * | 6/2006 | Kuracina et al. | 604/116 |
| 7,416,541 B2 | * | 8/2008 | Yuzhakov et al. | 604/272 |
| 2004/0019371 A1 | * | 1/2004 | Jaafar et al. | 607/50 |
| 2004/0116953 A1 | * | 6/2004 | Dixon | 606/186 |
| 2005/0203575 A1 | * | 9/2005 | Carson et al. | 606/204.35 |
| 2007/0073217 A1 | * | 3/2007 | James | 604/46 |
| 2007/0129714 A1 | * | 6/2007 | Elkins et al. | 606/21 |

OTHER PUBLICATIONS

Anastassakis, Dr. K. "Percutanous Delivery: The Dermaroller Series." May 2005.*

* cited by examiner

*Primary Examiner*—Todd E Manahan
*Assistant Examiner*—Erin Colello
(74) *Attorney, Agent, or Firm*—Dennis G LaPointe

(57) ABSTRACT

A skin rejuvenation resurfacing procedure comprising performing a punctile resurfacing procedure using a oscillating, reciprocating high speed, non-thermal, needle-based device for inducing mechanical trauma to an area of the skin to be treated.

12 Claims, 5 Drawing Sheets

SKIN REJUVINATION RESURFACING METHOD

FIELD OF THE INVENTION

The invention relates to a procedure using a punctile device in the field of aesthetic and reconstructive medicine and cosmetic surgery to enhance the appearance of skin wrinkles, skin texture and scars.

BACKGROUND OF THE INVENTION

The procedure referred to herein using punctile resurfacing was developed as a safe and effective skin rejuvenation system for the improvement of moderate wrinkles, scars, pores, pigmentation and skin texture.

In the aesthetic industry there are many procedures using devices that improve the appearance of the skin. These devices can be divided into laser, broad band light, mechanical and radiofrequency systems.

Lasers use specific wavelengths of light that penetrate the skin, bind to specific chromophores and, through a process called selective photothermolysis remove various colors and pigments from the skin. Other lasers with longer wavelengths of light enter the skin, cause nonspecific heating and improve the texture and fine wrinkling of the skin. Intense pulse light systems release many wavelengths of light at once and also improve the color and texture of the skin through selective photothermolysis. RadioFrequency technologies, use electrical current to heat the dermis (undercarpet of the skin) and stimulate some production of collagen and elastin Fibers that firm and tighten the skin. More ablative technology, $CO_2$ and Erbium laser resurfacing, chemical peels, plasma resurfacing and mechanical dermabrasion remove the outer layers of the skin, in a relatively precise fashion and through the natural healing process, new collagen and elastin is produced in the skin, improving wrinkles and texture.

Pin point, segmental or fractional injuries to the skin and dermis can be delivered by laser systems such as Fraxel™, which sends small beams of erbium glass laser wavelengths into the dermis or the Medical Roll CIT™, which is a hand held roller with widely spaced needles. The advantage of these segmental, fractional injury and puncturing procedures, is the dermis is stimulated with either a heat or mechanical trauma and the inflammatory response results in dermal remodeling and the production of new collagen, elastin and ground substance and ultimately, skin enhancement and rejuvenation.

The development of the device described herein and the punctile remodeling procedure was designed to deploy, through the proven efficacy of the fractional approach to dermal injury, remodeling and rejuvenation with a precision, high speed, mechanical needle puncture system and procedure that would safely and effectively improve the texture and appearance of skin with out the need for laser heating.

Industry and Device Comparisons

Monochromatic Lasers:

These devices use specific wavelengths of light that penetrate the skin, bind to specific chromophores and, through a process called selective photothermolysis, remove various colors and pigments from the skin. The lasers are large, expensive pieces of capital equipment, only attack specific problems or colors in the skin, are prone to laser burns, scars, can cause hyper and/or hypopigmentation and may result in user and patient ocular injuries.

Intense Broad Band Light Systems:

These systems emit multiple wavelengths of light, and through selective photothermolysis, also improve skin discoloration and, through skin heating, non-specific skin texture improvement. The systems are also larger and expensive, the skin textures and wrinkle improvements are minimal and there is also the risk of skin burns, hypo or hyperpigmentation and scars.

RadioFrequency Devices:

RadioFrequency technologies, use electrical current to heat the dermis (undercarpet of the skin) and stimulate some production of collagen and elastin fibers that firm and tighten the skin. The devices are relatively expensive, have only modest skin texture or wrinkle improvements, being more designed for modest skin tightening. There is also a risk of localized fat necrosis, with permanent dimpling, damage to sensory nerves and scarring.

Plasma Technology:

Plasma technologies use saline and electrical current to induce a thin burn on the outer surface of the skin, inducing a dermal injury which heals with increase collagen, elastin and dermal ground substance. Although these devices do produce a good improvement in wrinkles, skin tightening and texture, they are expensive pieces of capital equipment and also run the risk of scarring, hyper or hypopigmentation. The recovery from the procedure is characterized by oozing and discharge and patients are not ready for make up for 2 weeks.

Laser Resurfacing and Chemical Peel:

Carbon Dioxide or Erbium lasers are used to burn off the outer layer of skin inducing a thermal injury in the dermis which heals by remodeling and increased collagen and elastin production. Resurfacing lasers also produce good wrinkle and texture improvements with skin tightening, but are expensive can potentially cause scars and profound hypopigmentation and ocular injury and blindness to the user and the patient. The recovery from the procedure is characterized by oozing and discharge and patients are not ready for make up for 2 weeks.

Fraxel Laser:

Is a fractional dermal injury system that functions by emitting beams of erbium glass laser energy that creates multiple small holes in the dermis, alongside uninjured skin. The fractional dermal injury results in the remodeling without the significant recovery. The fraxel laser is expensive, and has modest results at best.

Medical Roll CIT:

This is also a fractional dermal injury system. It is a hand held roller with needles mounted on the roller. It is passed repeatedly by hand across the skin creating a dermal injury but leaving a large portion of the epidermis intake. There is some bruising and swelling, but very little pain, weeping or oozing. The mechanical injury to the dermis results in some structural collagen and elastic, smoothening out fine wrinkles. The needles are very long and widely spaced and the patients experience a significant amount of discomfort due to the length of the needle. The hand held nature of the device, make predictable spacing of the segmental injury imprecise.

What is needed is a procedure using a Pixelatory™ and Punctile Resurfacing device. The inventor herein has developed a more efficient, fast, predictable and less painful device and procedure than the above described Medical Roll CIT device and its procedure. The present inventive using the inventor's developed Pixelator™ device provides for a resulting dermal remodeling that improves fine to moderate wrinkles, pigmentation and obtains skin texture improvement. Because there is no laser or thermal component to the injury, there is very little risk of hypopigmentation or scarring.

SUMMARY OF THE INVENTION

The present invention is a procedure using a foot pedal controlled power source, that sends electrical energy to a reciprocating hand piece, that is, a hand piece that contains the equipment that causes the reciprocating and oscillating action of the device. The reciprocating hand piece provides the rapid oscillating, reciprocating back and forth ("in and out") motion of the needle tips. The tip of the reciprocator device has a screw on tip to which the needle tip attaches.

The working tip of the Pixelator™ reciprocator or needle-based device is the needle tip. It is a series of a number of needles in a desired array, typically 12 needles, two rows of 6 needles affixed in a rectangle, to a long stainless steel shaft and it screws onto the tip of the handpiece or headpiece. Other needle arrays are contemplated such as 8 needles up to 16 needles, with different configurations to the needle tips themselves.

The needle tip while reciprocating in and out rapidly will have some toggle and to prevent this, a sheath is inserted over the needle tip and a disposable plastic tip protector is inserted inside the sheath. The plastic tip can be pushed in or withdrawn to expose more or less of the needle tip. Thus, the plastic tip controls the depth of penetration.

The Pixelator™ needle-based device is a skin rejuvenation device that works on the principle of fractional dermal injury, but induced through a high speed, non-thermal, needle based mechanical trauma. Once the Midas headpiece is assembled, the plastic tip protector is advanced in or out of the sheath to set the length of the punctile needles that will be exposed to the skin during the treatment, providing a controllable "depth gauge" for the depth of dermal injury.

Anesthesia: The patient is usually anesthetized with local anesthesia. The upper and lower lips, lower eyelids, frown line region and any area of acne scarring can by infiltrated with local anesthesia and treated.

Punctile Resurfacing: The hand piece and tip is placed over the skin with direct contact of the needle tip with the skin. By depressing the foot pedal, the 40 Hz reciprocating oscillations ("in and out" motions of the needle tip) begin and with each reciprocation the needles penetrate into the dermis, according to the depth that was set on by the adjustment of the plastic tip protector. The Pixelator™ hand piece is then passed in one direction across the whole surface area to be treated. The movements are gentle but fast and move in one direction. Once one pass of the entire treatment area has been completed the hand piece and needle tip are then passed in the opposite direction, about 90 degrees to the first pass. Once this pass is completed a third pass is made 90 degrees to the previous pass. With this criss-crossing pattern, up 6-9 passes may be made in each treatment zone. With each pass there is a small amount of pin-point bleeding, which stops very quickly, due to the fractional nature of the injury and the presence of bridging epthermal skin segments. Most of the trauma is dermal and ecchymosis (bruising) is induced under the skin. It is the post dermal inflammation that will determine the level of new dermal substrate formation. After each pass, the small amount of blood residual on the surface is wiped off, clotting occurs very quickly and the next pass initiated.

Punctile Resurfacing End Point: After about 6-9 crisscrossing passes on the skin, there will be a deep bruised discoloration to the skin and edema. Once the ecchymotic, bruised discoloration and edema has eliminated or greatly reduced the wrinkle, scar or textural abnormality and the color of the dermal bruise is dark blue, the end point of treatment has arrived. Generally an upper lip or lower lid sized zone takes 10 minutes to reach the therapeutic end point.

Post-Punctile Resurfacing Care: As punctile resurfacing is a fractional injury, there is a microscopic but substantial area of the epidermis that is intact. The intact epidermis affects a very rapid hemostatic effect and re-epithelialization repair. As a consequence, the patients punctile resurfacing area, although bruised in appearance, exhibits minimal oozing and discomfort as the superficial epidermis is re-epithelialize within 24-48 hours. Cleansing with water and a topical emollient, such as Polysporin™ ointment is the only after care.

Punctile Resurfacing Results: Over the 6-12 weeks post-punctile resurfacing, the bruising and edema resolves in 4-5 days and the patient may wear makeup. By 3-4 months, the mechanical trauma and inflammation that was induced by the fractional needle punctures has induced and post inflammatory reaction resulting in new dermal collagen, elastin and ground substance production. The clinical results are smoother wrinkles, improvement in depressed scars, pores, brown discoloration and enhanced skin texture.

Features of the Pixelator™ needle-based device that are used and/or beneficial in the novel procedure are the more closely spaced needle configuration for more precise fractional dermal injury, the reciprocating mechanical handpiece for more rapid and predictable treatment of areas, the adjustable tip for more control over the depth of the dermal injury, the hand held, comfortable, light and 110-volt out of the wall power source (although DC current is also contemplated), the disposable needle tip and plastic tip guide, the device headpiece and sheath can be reused, the low cost of operation, the fact that the procedure does not use a laser device, making it safer for the operator and patient, and that there is little risk of scars or hypopigmenation as Pixelator™ needle-based device causes a non-thermal mediated injury.

The inventive procedure is a skin rejuvenation resurfacing procedure comprising performing a punctile resurfacing procedure using an oscillating, reciprocating high speed, non-thermal, needle-based device for inducing mechanical trauma to an area of the skin to be treated.

A desired number of passes are made over the surface area of the skin to be treated in a criss-crossing pattern until there is a deep bruised discoloration and edema to the area of the skin being treated such that a wrinkle, scar or textural abnormality being treated has been eliminated or greatly reduced.

After the procedure is completed using the needle-based device, the area of the skin treated is cleansed and a topical emollient is applied.

The resultant bruising and edema resolves in 4-5 days such that make-up may be worn on the treated area, and the mechanical trauma and inflammation that was induced by fractional needle punctures and the post inflammatory reaction results in new dermal collagen, elastin and ground substance production thereby resulting in smoother wrinkles, improvement in depressed scars and enhanced skin texture.

Prior to starting the resurfacing treatment, the patient being treated is anesthetized with local anesthesia to the area of the skin to be treated.

DETAILED DESCRIPTION OF THE INVENTION

Figure 1:
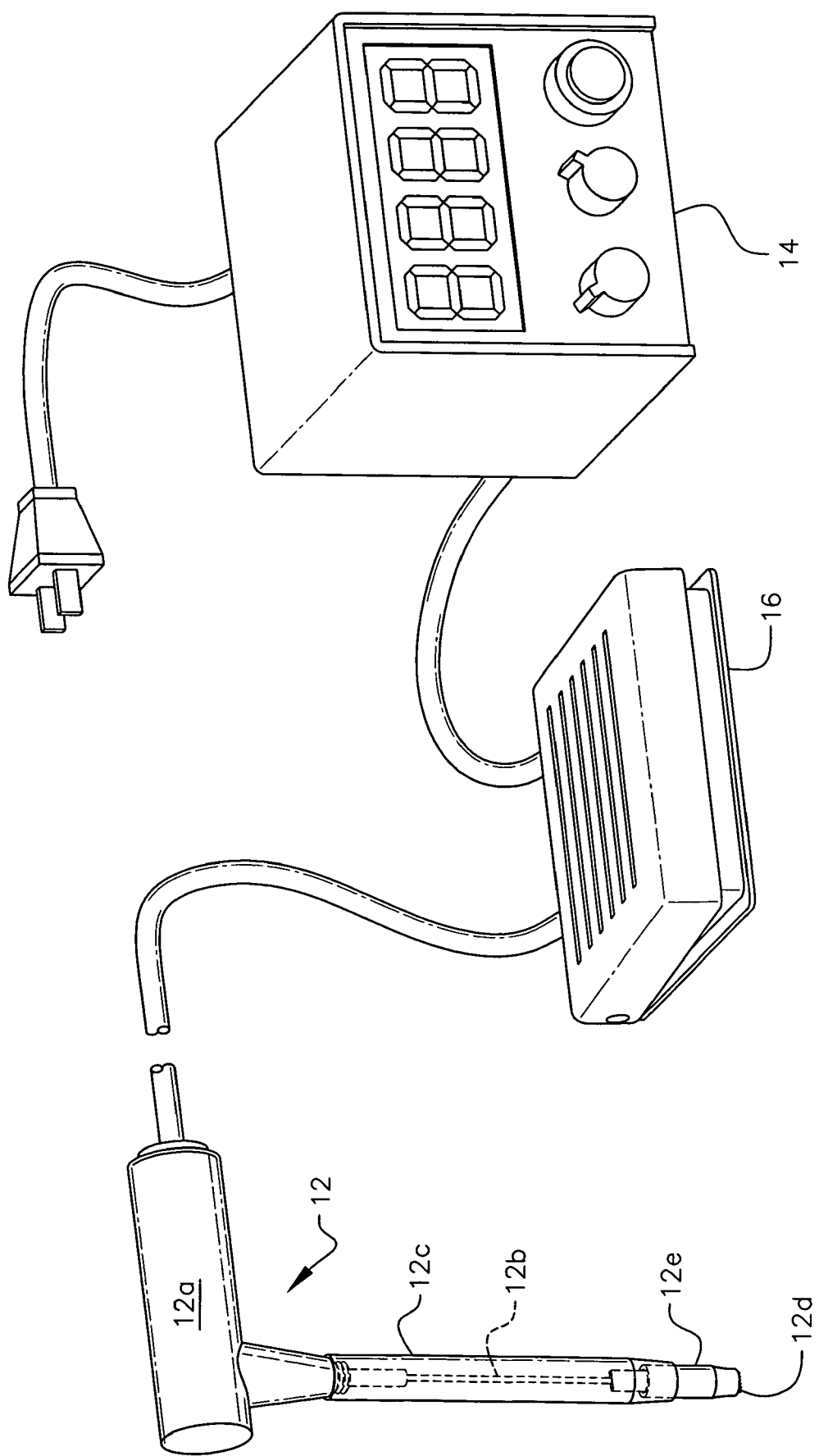
FIG. 1 is a schematic depiction of one example of the major system components used in the inventive procedure.

Referring now to the drawings, FIGS. 1, 2A, 2B, 3, 4A and 4B disclose an example of the major system components used in the inventive procedure. Reference to these components will be made in describing the inventive procedure.

The invention is a skin rejuvenation resurfacing procedure wherein a punctile resurfacing procedure is performed on a subject patient using an oscillating, reciprocating high speed, non-thermal, needle-based device 12 for inducing mechanical trauma to an area of the skin to be treated. Prior to commencing the procedure, the patient being treated is anesthetized with local anesthesia to the area of the skin to be treated.

A desired number of passes are made over the surface area of the skin to be treated in a criss-crossing pattern until there is a deep bruised discoloration and edema to the area of the skin being treated such that a wrinkle, scar or textural abnormality being treated has been eliminated or greatly reduced.

The skin area to be treated is treated using the needle-based device 12 by passing in a first direction. Then an alternating pass is done in a generally criss-crossing pattern to the first direction and the treatment is repeated in this alternating criss-crossing pattern. The typical desired number of passes made over the area of the skin to be treated in the criss-crossing pattern is six to nine passes in each direction of the criss-crossing pattern.

After this step is completed, the area of the skin treated is cleansed and a topical emollient, such as Polysporin™ antibacterial ointment is applied.

The resultant bruising and edema resolves in 4-5 days such that make-up may be worn on the treated area, and the mechanical trauma and inflammation that was induced by fractional needle punctures and the post inflammatory reaction results in new collagen, elastin and ground substance production thereby resulting in smoother wrinkles, improvement in depressed scars, lessened pigmentation and enhanced skin texture.

The needle-based device 12 is a hand-held device and is the power is controlled by a hands-free means. For example, a foot pedal or foot control switch 16 is typically used in the control circuit between a power controller source 14 and the hand-held needle-based device 12. The power controller source is depicted in FIG. 1 as being powered by an alternating current source but alternatively could be powered by a direct current source.

Figure 2A:
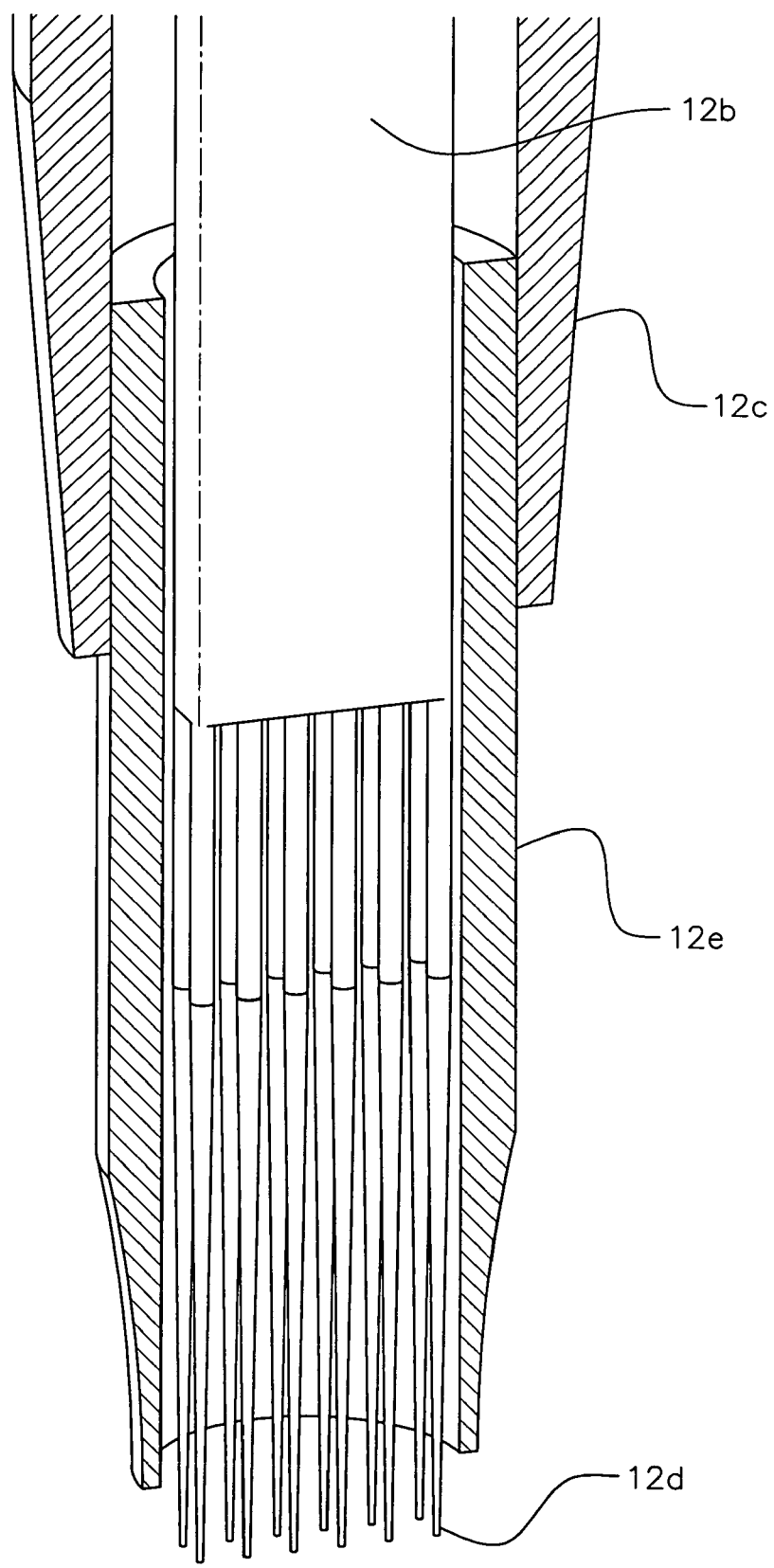
FIG. 2A is a cross-sectional view of the needle tip area.
Figure 2B:
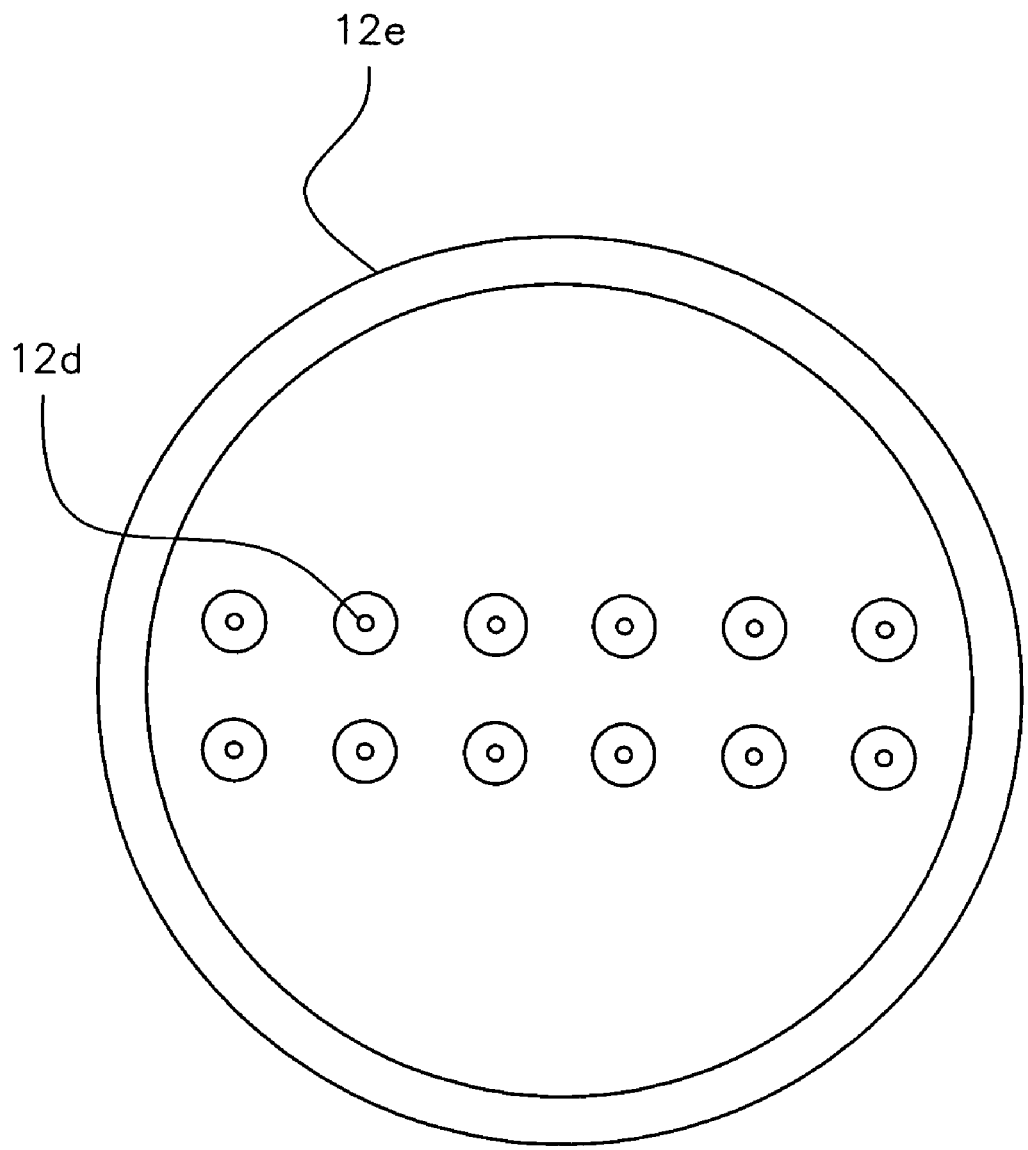
FIG. 2B is an end view of the needle tip area of FIG. 2A.
Figure 3:
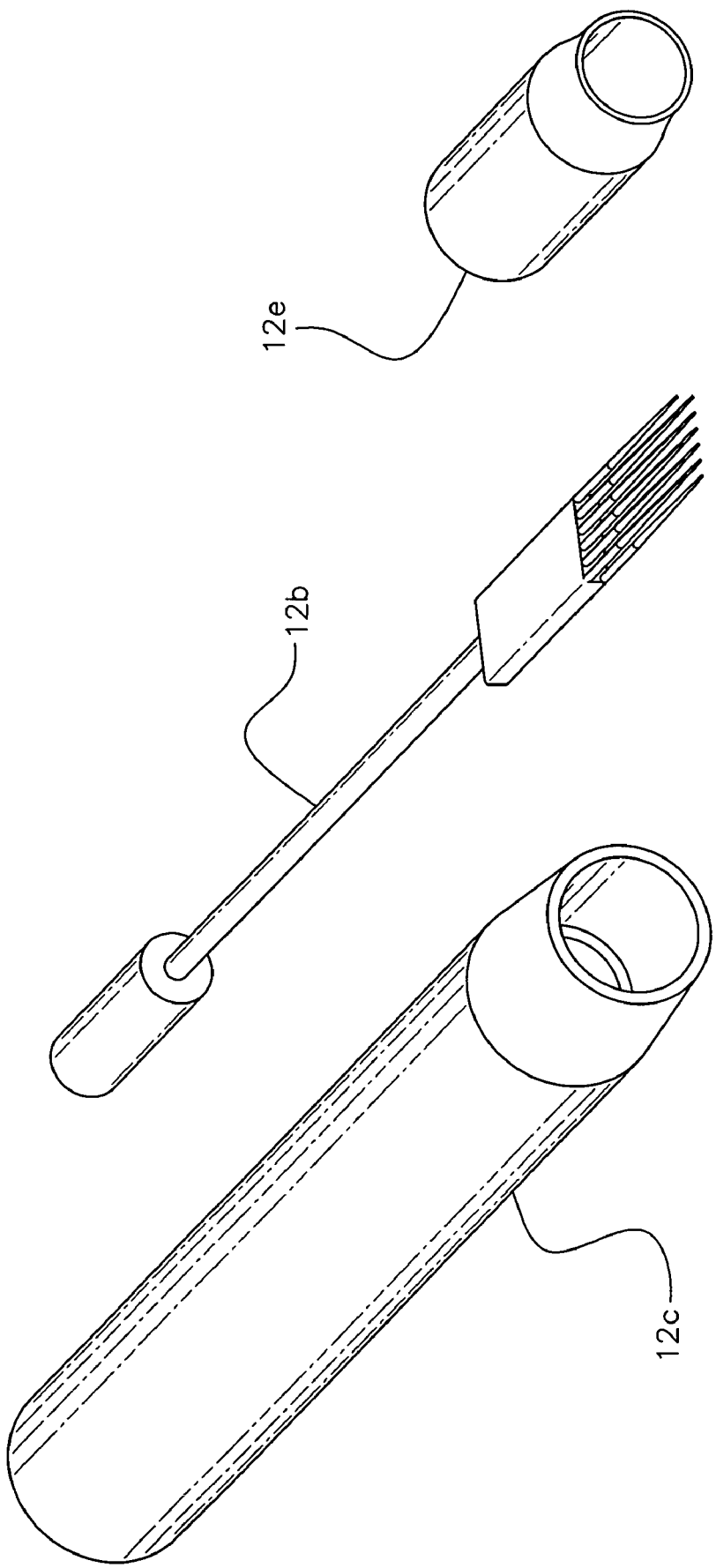
FIG. 3 is a depiction of a typical needle, needle tip sheath and needle tip plastic protector.
Figure 4A:
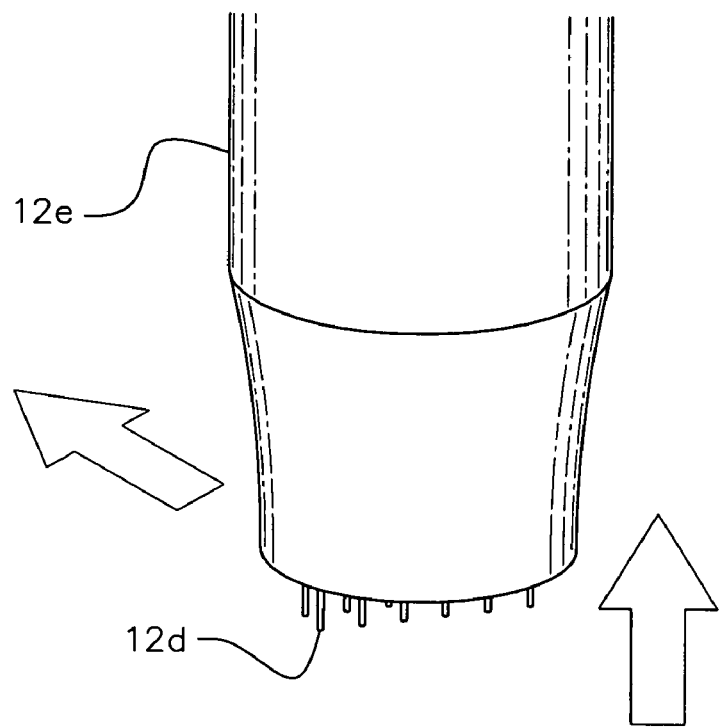
FIG. 4A is a depiction of the end of the needle tip area being directed in a path with the needles in a partially retracted position.
Figure 4B:
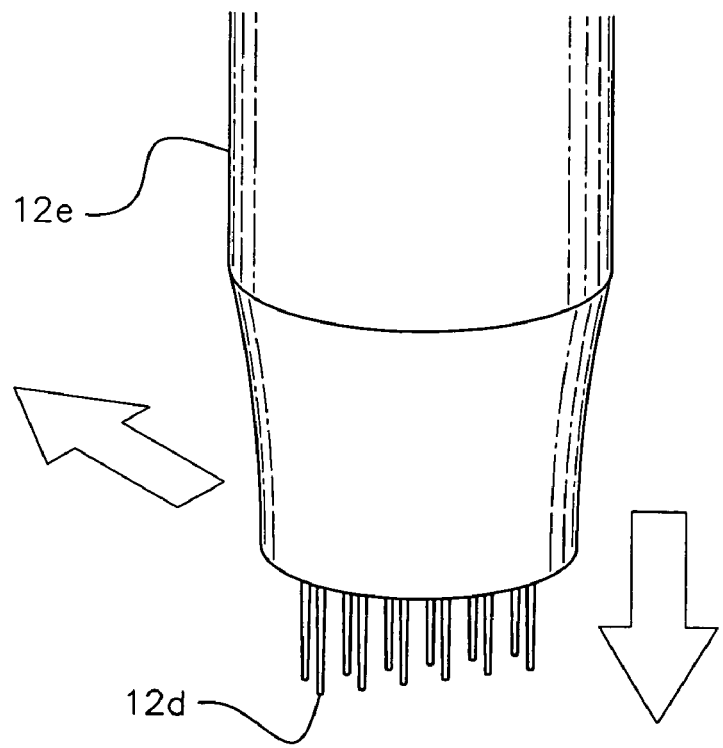
FIG. 4B is a depiction similar to FIG. 4A with the needles in an extended position.

The needle-based device includes needle depth adjustment means for obtaining a desired skin penetration depth of needle tip 12b of a plurality of needles 12d for the appropriate treatment of the area of the skin being treated. The plurality of needles 12d are preferably arranged in an array comprising between eight to sixteen needles. For example, FIG. 2b depicts an array of 12 needles arranged in a 2×6 configuration.

The needle-based device 12 comprises a hand-held portion 12a housing means for oscillating and reciprocating an elongate needle portion 12b. This a commercially available hand piece, also referred to as head piece, which houses the motor and oscillating means (not shown) and to which the elongate needle portion 12b is connected at one end and in mechanical communication with the means for oscillating and reciprocating said needle portion 12b. Typically, the needles 12d oscillate/reciprocate at about 40 cycles per second.

As mentioned above, the elongate needle portion 12b has at its opposite end, a plurality of needles 12d configured in a desired array, such as 2×6.

A needle sheath 12c is provided to slide over the needle portion 12b and attach to the hand piece 12a. The attachment can be by threaded means or other methods known in the art. Sheath 12c generally covers the elongate needle portion 12b and is connected to the hand-hand portion 12a and ends with the array of the plurality of needles 12d. The needle sheath 12c further serves as means for preventing a side to side movement of the elongate needle portion 12b.

A needle tip protector 12e is attached over the plurality of needles 12d and is slidably operable over the plurality of needles 12d for serving as the needle depth adjustment means for obtaining the desired depth of needle penetration of said needle tips to the skin area being treated. Typically, the protector is slidably engaged with the end of the sheath 12c and is pushed into or pulled away from the end of the sheath 12c so that when the needle tips are extended at the maximum reciprocation distance away from hand piece 12a, the distance between the tips and the protector edge equates to the maximum penetration depth desired to accomplish the desired treatment.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

The invention claimed is:

1. A skin rejuvenation resurfacing procedure comprising the steps of:
   anesthetizing with local anesthesia an area of a patient's skin to be transdermally treated prior to the beginning of the resurfacing procedure;
   inducing a mechanical trauma transdermally into the epidermis, dermis and subcutaneous fat by using an oscillating, reciprocating high speed, non-thermal, needle-based device operated at about 40 cycles per second to induce a purposeful full skin thickness injury and inflammatory response that leads to collagen, elastic and ground substances to resurface said patient's skin,
   wherein a desired number of passes are made over the surface area of the skin being treated in a criss-crossing pattern or generally circular pattern until there is a deep bruised discoloration to the dermis and edema to the area of the skin being transdermally treated,
   continuing said procedure until a fraction of the dermis has been mechanically and fractionally abraded and ablated leading to a regeneration and renewal of the epidermal surface and stratum corneum,
   wherein the needle-based device includes needle depth adjustment means for obtaining a desired transdermal penetration needle tip depth sufficient to penetrate through said epidermis, dermis and into said subcutaneous fat of needle tips of a plurality of needles for the appropriate treatment of the area of the skin being treated, and wherein the needle-based device further comprises:
- a hand-held portion comprising means for oscillating and reciprocating an elongated needle portion,
- an elongated needle portion being connected at one end to said hand-held portion and in mechanical communication with said means for oscillating and reciprocating said needle portion,
- the elongated needle portion having at its opposite end, the plurality of needles configured in a desired array.

2. The procedure according to claim 1, wherein the area of the skin being treated is one of the group consisting of a wrinkle, scar, pore, brown pigmentation, and textural abnormality.

3. The procedure according to claim 2, further comprising cleansing the area of the skin treated and applying a topical emollient after the treatment is completed.

4. The procedure according to claim 3, when the resultant bruising and edema resolves such that make-up may be worn on the treated area, and the mechanical trauma and inflammation that was induced by fractional needle punctures and the post inflammatory reaction results in new dermal collagen, elastin and ground substance production thereby resulting in smoother wrinkles, improvement in depressed scars and enhanced skin texture.

5. The procedure according to claim 1, wherein the needle-based device is a hand-held, mechanical device and is controlled by hands-free means.

6. The procedure according to claim 5, wherein the hands-free means for controlling the needle-based device is a foot control switch between a power controller source and the hand-held needle-based device.

7. The procedure according to claim 1, wherein the plurality of needles are arranged in an array comprising between eight to sixteen needles.

8. The procedure according to claim 1, wherein the needle-based device further comprises:
- a needle sheath generally covering said elongate needle portion and connected to the hand-hand portion and ending near the plurality of needles, said needle sheath further serving as means for preventing a side to side movement of the elongate needle portion; and
- a needle tip protector attached over the plurality of needles, said needle tip protector being slidably operable over the plurality of needles for serving as the needle depth adjustment means for obtaining the desired depth of needle penetration of said needle tips to the skin area being treated.

9. The procedure according to claim 8, wherein the plurality of needles are arranged in an array comprising between eight to sixteen needles.

10. The procedure according to claim 9, comprising twelve needles.

11. The procedure according to claim 1, the skin area to be treated is treated using the needle-based device by passing in a first direction, then an alternating pass is done in a generally criss-crossing pattern to said first direction and said treatment is repeated in said alternating criss-crossing pattern.

12. The procedure according to claim 11, wherein the desired number of passes made over the area of the skin to be treated in the criss-crossing pattern is six to nine passes in each direction of the criss-crossing pattern.

* * * * *